(12) United States Patent
Jung et al.

(10) Patent No.: US 12,357,238 B2
(45) Date of Patent: Jul. 15, 2025

(54) BLOOD PRESSURE ESTIMATION METHOD USING CASCADE FOREST REGRESSION MODEL

(71) Applicant: Industry-Academic Cooperation Foundation, Chosun University, Gwangju (KR)

(72) Inventors: Jae Hyo Jung, Gwangju (KR); Geng Jia Zhang, Gwangju (KR); Dae Gil Choi, Gwangju (KR)

(73) Assignee: Industry-Academic Cooperation Foundation, Chosun University, Gwangju (KR)

(*) Notice: Subject to any disclaimer, the term of this patent is extended or adjusted under 35 U.S.C. 154(b) by 60 days.

(21) Appl. No.: 18/512,153

(22) Filed: Nov. 17, 2023

(65) Prior Publication Data

US 2025/0009309 A1  Jan. 9, 2025

(30) Foreign Application Priority Data

Jul. 5, 2023  (KR) .......................... 10-2023-0087370

(51) Int. Cl.
*A61B 5/00* (2006.01)
*A61B 5/021* (2006.01)
*A61B 5/026* (2006.01)
*G16H 50/30* (2018.01)

(52) U.S. Cl.
CPC ............ *A61B 5/7267* (2013.01); *A61B 5/021* (2013.01); *A61B 5/0261* (2013.01); *A61B 5/7278* (2013.01); *G16H 50/30* (2018.01)

(58) Field of Classification Search
CPC ..... A61B 5/7267; A61B 5/021; A61B 5/0261; A61B 5/7278; A61B 5/02108; A61B 5/02416; A61B 5/7207; A61B 5/7264; A61B 5/7275; G16H 50/30; G16H 50/20; G16H 50/50

See application file for complete search history.

(56) References Cited

U.S. PATENT DOCUMENTS

| 9,788,794 | B2* | 10/2017 | LeBoeuf ............... A61B 5/4205 |
| 10,201,312 | B2* | 2/2019 | Kumar ................... A61B 5/02 |
| 10,959,681 | B2* | 3/2021 | Selvaraj ................. A61B 7/00 |
| 2016/0166160 | A1* | 6/2016 | Casale ............... A61B 5/0295 600/480 |
| 2019/0159735 | A1* | 5/2019 | Rundo ................... A61B 5/168 |

* cited by examiner

*Primary Examiner* — Bo Joseph Peng
(74) *Attorney, Agent, or Firm* — Studebaker Brackett PLLC (57) ABSTRACT

The present invention relates to a method for estimating blood pressure from photoplethysmography (PPG) signals. The blood pressure estimation method using the CFR model according to an embodiment of the present invention is characterized in that it comprises the steps of extracting a plurality of blood flow characteristics from PPG signals for training, calculating systolic and diastolic blood pressures from ambulatory blood pressures for training, labeling the systolic and diastolic blood pressures with the plurality of blood flow characteristics to train a cascade forest regression model, and inputting the PPG signals of a target user into the trained cascade forest regression model to determine the systolic and diastolic blood pressures of the target user.

12 Claims, 9 Drawing Sheets

BLOOD PRESSURE ESTIMATION METHOD USING CASCADE FOREST REGRESSION MODEL

CROSS-REFERENCE TO RELATED APPLICATIONS

This application claims the priority of Korean Patent Application No. 10-2023-0087370 filed on Jul. 5, 2023, in the Korean Intellectual Property Office, the disclosure of which is incorporated herein by reference.

BACKGROUND OF THE INVENTION

Field of the Invention

The present invention relates to a method for estimating blood pressure from photoplethysmography (PPG) signals.

Description of the Related Art

High blood pressure is the cause of various cardiovascular and cerebrovascular diseases such as stroke, myocardial infarction and heart failure, and statistical data on causes of death in 2022 announced by the National Statistical Office of Korea showed that 4 out of top 10 causes of death were cardiovascular diseases (e.g., heart diseases, cerebrovascular diseases, diabetes and hypertensive diseases).

Since cardiovascular diseases are mainly caused by blockage of blood flow due to vascular stenosis, it is very important to monitor blood pressure to prevent diseases, and, for this purpose, equipment based on oscillometric principles has been used.

Typically, an automatic blood pressure monitor based on the oscillometric principle uses the method of applying pressure to a user's arm through a cuff to block the blood flowing into the user's arm, and then gradually release the pressure on the cuff to measure the blood pressure depending on the amount of pressure applied to the cuff.

Although this method is widely used because it is easy to measure and has high accuracy, it has the problems that it causes discomfort to users by applying pressure to the body, requires a break of at least 1 minute for repeated measurements, and uses bulky and expensive equipment such that users may not substantially perform self-measurement in their daily lives.

Accordingly, there is a need for a methodology that can easily monitor blood pressure in a non-invasive manner.

SUMMARY OF THE INVENTION

The present invention aims to estimate blood pressure from PPG signals by using a cascade forest regression (CFR) model.

The objectives of the present invention are not limited to the objectives mentioned above, and other objectives and advantages of the present invention that are not mentioned can be understood by the following description and will be more clearly understood by the examples of the present invention. Further, it will be readily apparent that the objectives and advantages of the present invention can be practiced by the means and combinations thereof recited in the claims.

The blood pressure estimation method using the cascade forest regression model according to an embodiment of the present invention to achieve the above-described objectives comprises the steps of extracting a plurality of blood flow characteristics from PPG signals for training, calculating systolic and diastolic blood pressures from ambulatory blood pressures for training, labeling the systolic and diastolic blood pressures with the plurality of blood flow characteristics to train a cascade forest regression model, and inputting the PPG signals of a target user into the trained cascade forest regression model to determine the systolic and diastolic blood pressures of the target user.

In one embodiment, the step of extracting a plurality of blood flow characteristics comprises passing the PPG signals for training through a high pass filter (HPF) to remove noise from the PPG signals for training.

In one embodiment, the step of extracting a plurality of blood flow characteristics comprises sampling the PPG signals for training at unit time intervals, detecting R-R interval and heart rate variability (HRV) from the sampled signals, and extracting the plurality of blood flow characteristics based on the R-R interval and heart rate variability.

In one embodiment, the plurality of blood flow characteristics comprise BPM, SDNN, RMSSD, IBI and SDSD defined by [Table 1] below.

TABLE 1

| Blood characteristic | Definition |
| --- | --- |
| BPM | $\dfrac{60000 \text{ ms}(1 \text{ minute})}{\overline{RR}}$ |
| SDNN | $\sqrt{\dfrac{1}{n-1}\sum_{i=1}^{n}(RR_i - \overline{RR})^2}$ |
| RMSSD | $\sqrt{\dfrac{1}{n-1}\sum_{i=1}^{n}(RRdiff_i)^2}$ |
| IBI | $\dfrac{1}{n-1}\sum_{i=1}^{n} RR_i$ |
| SDSD | $\sqrt{\dfrac{1}{n-1}\sum_{i=1}^{n}(RRdiff_i - \overline{RRdiff})^2}$ |

(wherein $RR_i$ is the sequentially indexed R-R interval in the sampled signal, n is the number of $RR_i$ in the sampled signal, and $RRdiff_i$ is the heart rate variability sequentially indexed in the sampled signal.)

In one embodiment, the plurality of blood flow characteristics further comprise at least one of SD1, SD2, S, SD, pNN20, pNN50 and HR mad defined by [Table 2] below.

TABLE 2

| Blood characteristic | Definition |
| --- | --- |
| SD1 | $\sqrt{\dfrac{1}{2}SDSD^2}$ |
| SD2 | $\sqrt{2SDNN^2 - \dfrac{1}{2}SDSD^2}$ |
| S | $\pi \times SD1 \times SD2$ |
| SD | SD1/SD2 |
| pNNxx | $\dfrac{RR_x}{n}$ |
| HR mad | median(|$RR_i$ − median(RR)|) |

(wherein $RR_x$ is the number of $RR_i$ with an interval of x or more.)

In one embodiment, the step of calculating the systolic and diastolic blood pressures comprises sampling the ambulatory blood pressures for training at unit time intervals, detecting a plurality of high peaks and a plurality of low peaks in the sampled signals, and averaging out the plurality of high peaks and the plurality of low peaks, respectively, to calculate the systolic and diastolic blood pressures.

In one embodiment, the step of detecting the plurality of high peaks and the plurality of low peaks comprises detecting only peaks above a reference value.

In one embodiment, the step of training the cascade forest regression model comprises inputting the plurality of blood flow characteristics into the cascade forest regression model, and supervising training the cascade forest regression model such that the difference between the predicted values output from the cascade forest regression model and the labeled systolic and diastolic blood pressures is minimized.

In one embodiment, the cascade forest regression model comprises a plurality of layers, and each of the plurality of layers comprises a plurality of random forests and a plurality of extra trees.

In one embodiment, the cascade forest regression model is characterized in that it comprises a plurality of sequentially connected layers, and the predicted values output from the previous layer is combined with the blood flow characteristics and input into the next layer.

In one embodiment, the cascade forest regression model comprises a plurality of sequentially connected layers, and the step of training the cascade forest regression model comprises calculating the accuracy of the cascade forest regression model through a validation dataset comprising a portion of the PPG signals for training and a portion of the ambulatory blood pressures for training, and adding a layer to the cascade forest regression model if the accuracy is less than a reference value.

In one embodiment, the step of determining the systolic and diastolic blood pressures of the target user comprises collecting the PPG signals of the target user, sampling the PPG signal at unit time intervals, inputting the sampled signal into the cascade forest regression model, and determining the predicted values output from the cascade forest regression model as the systolic and diastolic blood pressures of the target user.

The present invention can estimate blood pressure from PPG signals by using a cascade forest regression (CFR) model, allowing users to self-measure blood pressure in a non-invasive and easy manner in their daily lives.

In addition to the above-described effect, specific effects of the present invention are described below, together with explanation of specific details for practicing the invention.

DETAILED DESCRIPTION OF THE PREFERRED EMBODIMENT

The above-mentioned objectives, features, and advantages will be described in detail below with reference to the accompanying drawings, so that those skilled in the art will be able to easily implement the technical idea of the present invention. In describing the present invention, if it is determined that a detailed description of known technologies related to the present invention may unnecessarily obscure the gist of the present invention, the detailed description will be omitted. Hereinafter, preferred embodiments according to the present invention will be described in detail with reference to the accompanying drawings. In the drawings, identical reference numerals are used to indicate identical or similar components.

In this specification, first, second, etc. are used to describe various components, but, of course, these components are not limited to these terms. These terms are merely used to distinguish one component from another component, and, unless specifically stated to the contrary, a first component may also be a second component.

Further, in the specification of the present invention, the arrangement on the "top (or bottom)" or on the "top (or bottom)" of a component means either that any component may be disposed in contact with the top (or bottom) of the component, or that another component may be interposed between the component and any component disposed on (or under) the component.

Further, when the specification of the present invention describes a component as being "connected," "coupled," or "connected" to another component, it should be understood either that the components may be directly connected or connected to each other, but another component may be "interposed" between the components, or that the components may be "connected," "coupled," or "connected" through another component.

Further, as used herein, singular expressions comprise plural expressions, unless the context clearly dictates otherwise. As used herein, terms such as "consists of" or "comprises" should not be construed as necessarily comprising all of the various components or steps described in the specification. Further, it should be interpreted that some of the components or steps may not be contained, or additional components or steps may be contained.

Further, when the specification of the present invention describes "A and/or B," this means A, B, or A and B, unless otherwise specified. And when it describes "C to D," this means C or more and D or less, unless otherwise specified.

The present invention relates to a method for estimating blood pressure from photoplethysmography (PPG) signals by using a cascade forest regression (CFR) model. Hereinafter, a blood pressure estimation method using a cascade forest regression model (hereinafter referred to as a blood pressure estimation method) according to an embodiment of the present invention will be described in detail with reference to FIGS. 1 to 7.

Figure 1:
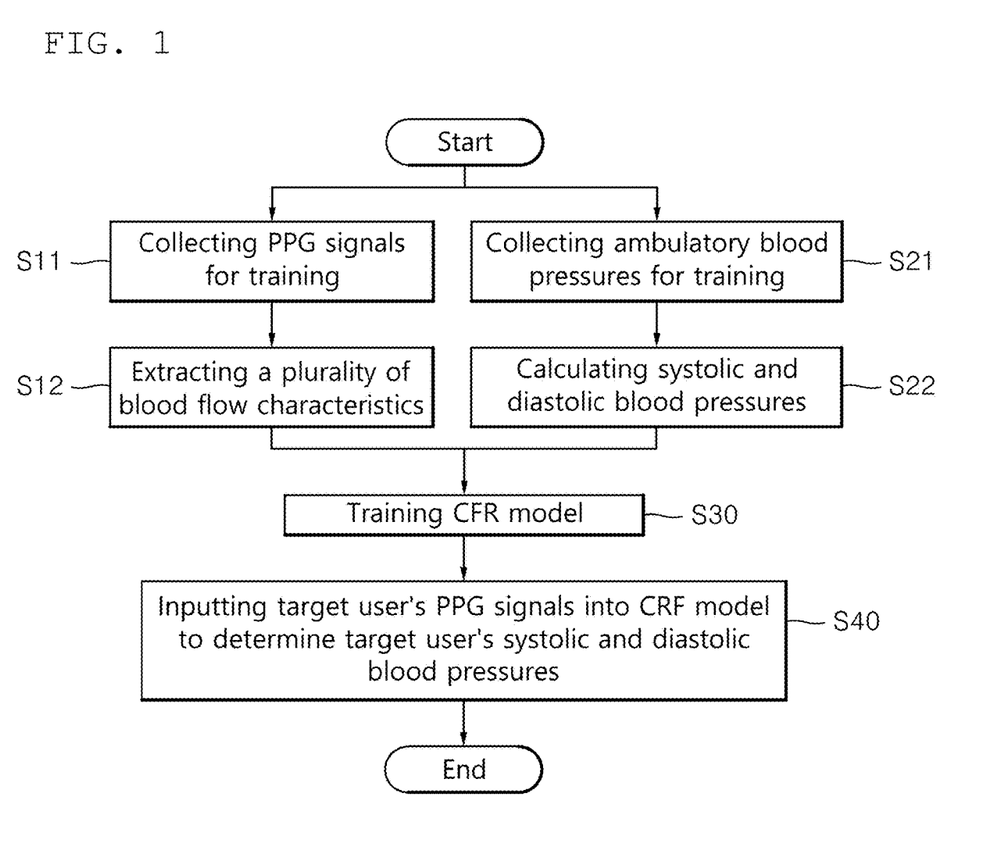
FIG. 1 is a flow chart illustrating a blood pressure estimation method using a cascade forest regression model according to an embodiment of the present invention.

FIG. 1 is a flow chart illustrating a blood pressure estimation method using a cascade forest regression model according to an embodiment of the present invention.

Figure 2A:
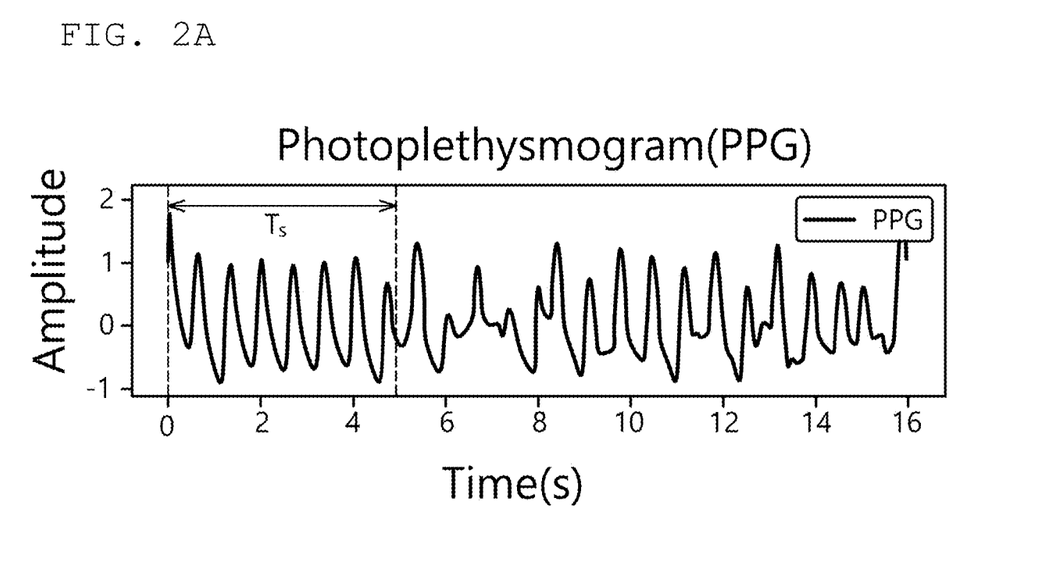
FIGS. 2A and 2B are diagrams showing the PPG signal and ambulatory blood pressure, respectively, used as training data for the cascade forest regression model.
Figure 2B:
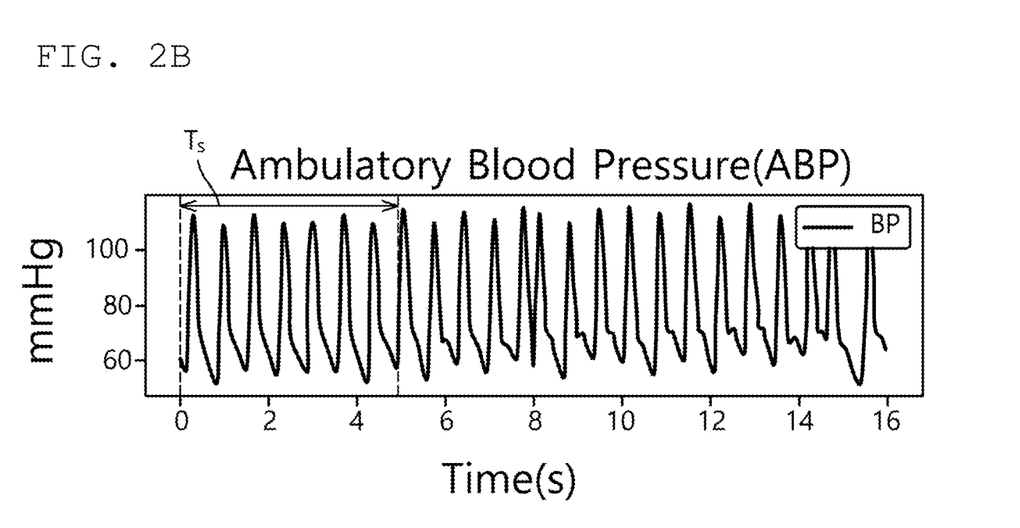

FIGS. 2A and 2B are diagrams showing the PPG signal and ambulatory blood pressure, respectively, used as training data for the cascade forest regression model.

Figure 3:
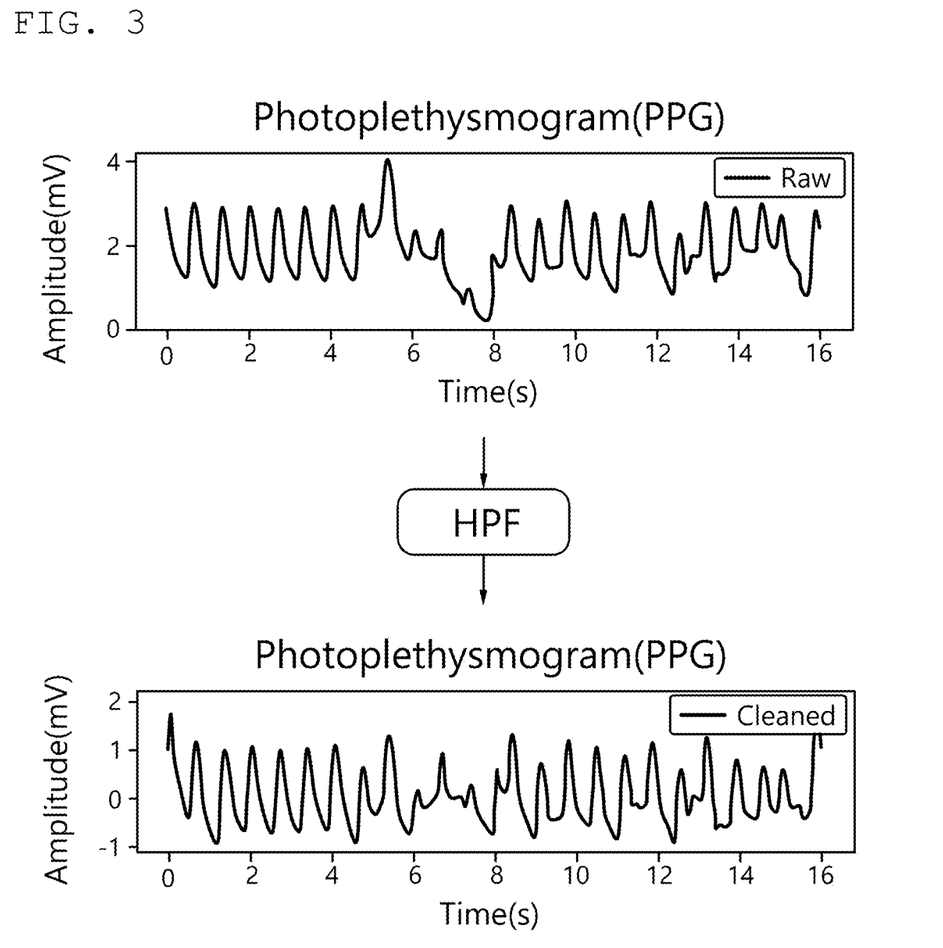
FIG. 3 is a diagram showing noise removal from a PPG signal using a high-pass filter.

FIG. 3 is a diagram showing noise removal from a PPG signal using a high-pass filter.

Figure 4:
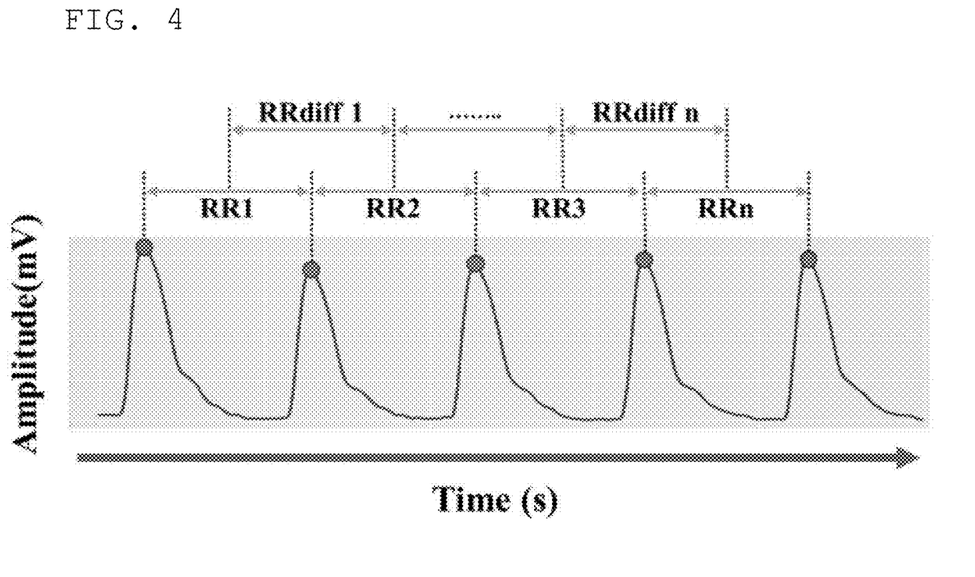
FIG. 4 is a diagram for explaining a method of detecting R-R interval and heart rate variability from a PPG signal.

FIG. 4 is a diagram for explaining a method of detecting R-R interval and heart rate variability from a PPG signal.

Figure 5A:
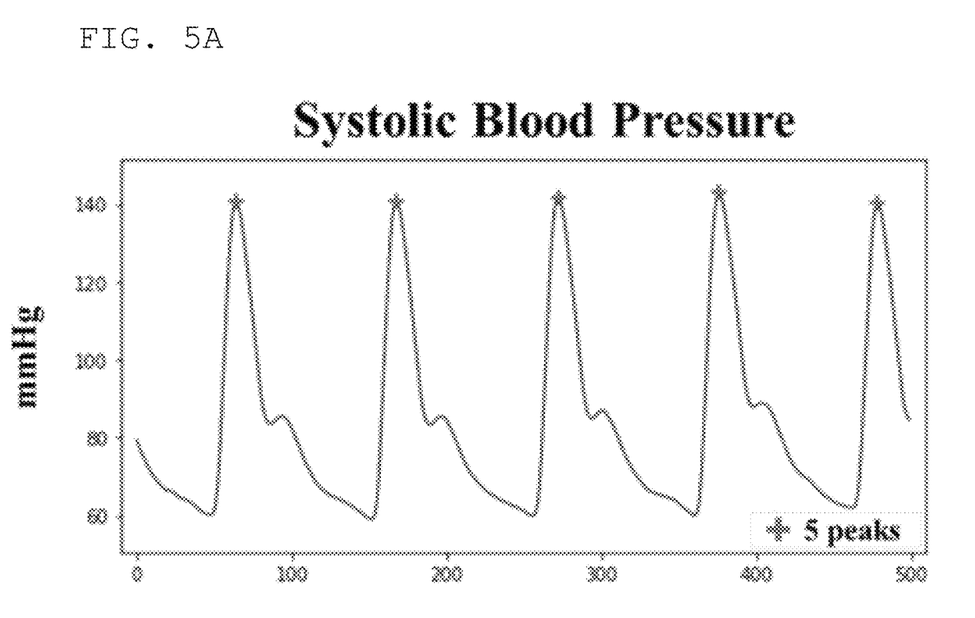
FIGS. 5A and 5B are diagrams for explaining a method of calculating systolic and diastolic blood pressures from ambulatory blood pressure.
Figure 5B:
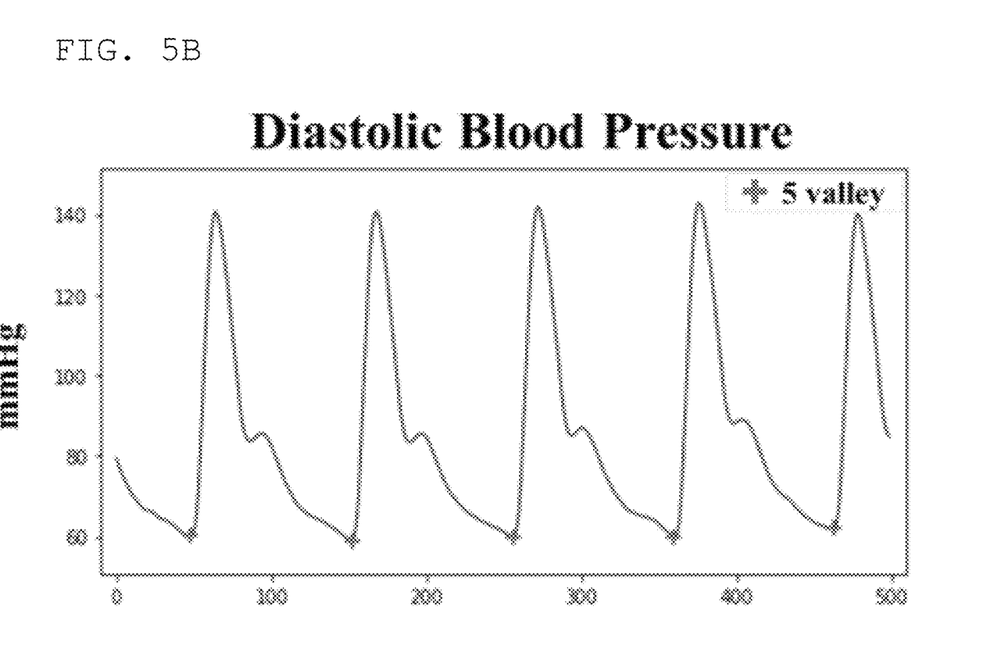

FIGS. 5A and 5B are diagrams for explaining a method of calculating systolic and diastolic blood pressures from ambulatory blood pressure.

Figure 6:
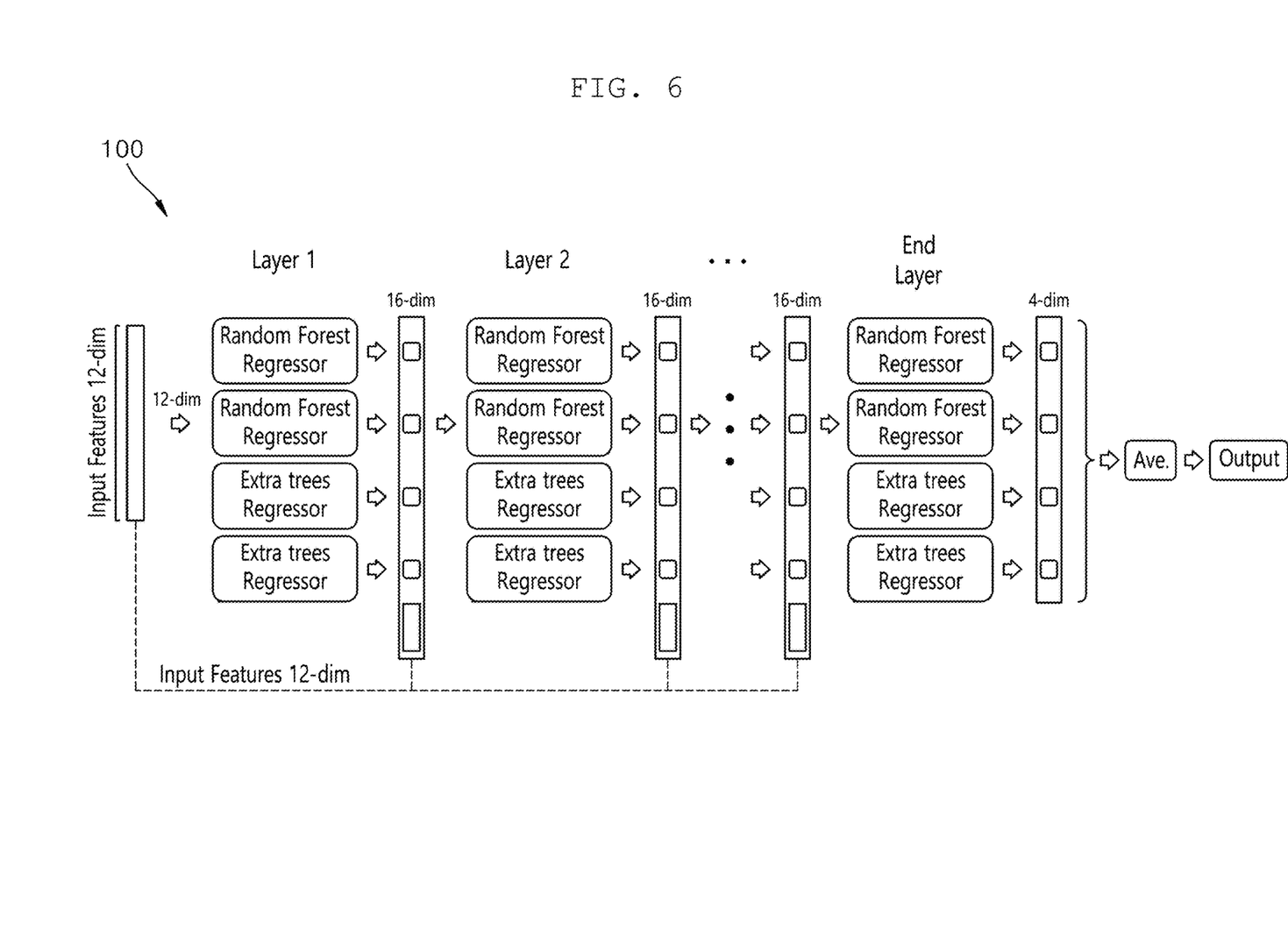
FIG. 6 is a diagram showing the structure of a cascade forest regression model according to an embodiment of the present invention.

FIG. 6 is a diagram showing the structure of a cascade forest regression model according to an embodiment of the present invention.

Figure 7:
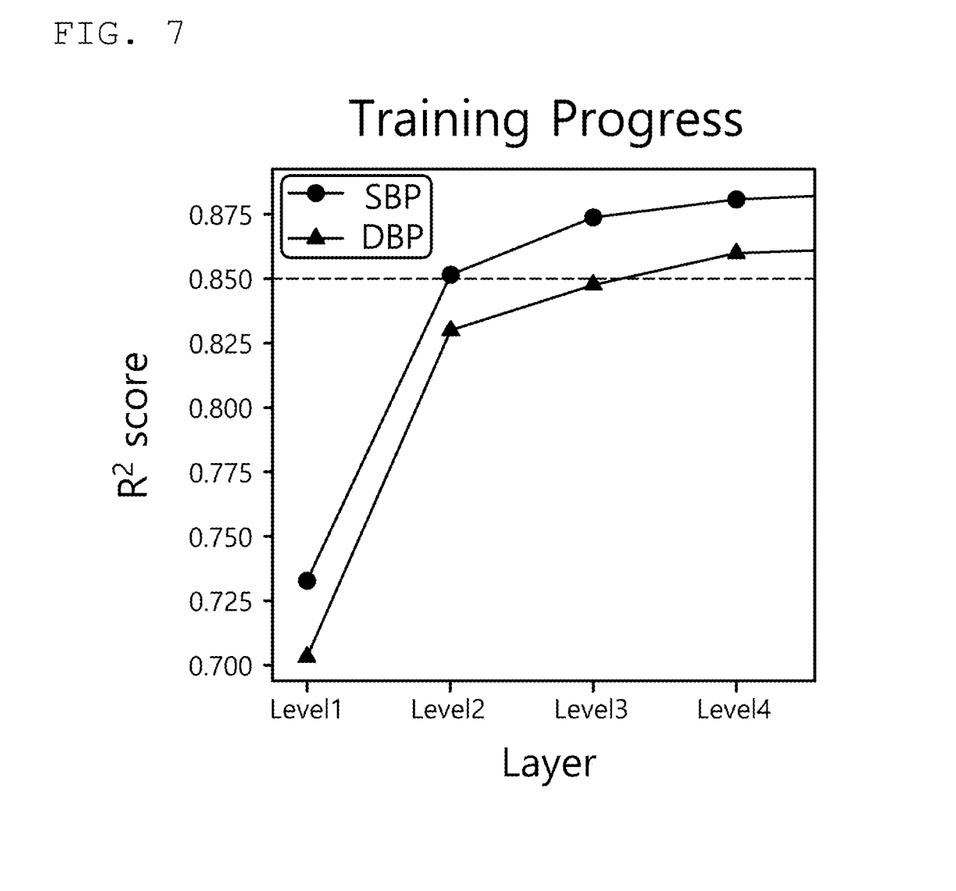
FIG. 7 is a graph showing prediction accuracy according to the number of layers in the cascade forest regression model.

FIG. 7 is a graph showing prediction accuracy according to the number of layers in the cascade forest regression model.

Referring to FIG. 1, the blood pressure estimation method according to an embodiment of the present invention may comprise the steps of collecting PPG signals for training and ambulatory blood pressures for training S11 and S21, extracting a plurality of blood flow characteristics from the PPG signals for training S12, and calculating systolic and diastolic blood pressures from the ambulatory blood pressures for training S22, training a cascade forest regression (CFR) model based on multiple blood flow characteristics and systolic and diastolic blood pressures S30, and inputting the target user's PPG signals into the CRF model to determine the target user's systolic and diastolic blood pressures S40.

However, the blood pressure estimation method shown in FIG. 1 is according to one embodiment, and each step of the invention is not limited to the embodiment shown in FIG. 1, and some steps may be added, changed, or deleted as necessary.

Each step shown in FIG. 1 may be performed by a processor, and, for this purpose, the processor may comprise at least one physical element among application specific integrated circuits (ASICs), digital signal processors (DSPs), digital signal processing devices (DSPDs), programmable logic devices (PLDs), field programmable gate arrays (FPGAs), micro-controllers, and a controller.

Hereinafter, each step shown in FIG. 1 will be described in detail.

The processor may collect PPG signals for training and ambulatory blood pressures for training as a training dataset for training the cascade forest regression (CFR) model described below S11 and S21.

Specifically, the processor may collect PPG signals and ambulatory signals for training measured over the same period of time for the same subject from a pre-built database. In the present invention, the database may be, for example, a Medical Information Mart for Intensive Care (MIMIC) database that stores patient biosignal data collected in an intensive care unit.

The processor may extract a plurality of blood flow characteristics from the PPG signals for training S12. Further, the processor may calculate systolic and diastolic blood pressures from the ambulatory signals for training S22.

Referring to FIG. 2A, the PPG signal indicates a measured degree to which the intensity changes due to blood flow when light irradiated on the skin is reflected, and may comprise various information related to blood flow. Specifically, the PPG signals for training may have periodicity according to the heartbeat when viewed macroscopically and may have intensity changes according to various non-linear blood flow characteristics when viewed microscopically.

Referring to FIG. 2B, ambulatory blood pressure (ABP) indicates a measured blood pressure during daily activities and may comprise information on systolic and diastolic blood pressures from which the white coat effect removed. Accordingly, ambulatory blood pressure may function as a label in the training of a CFR model, which will be described below.

Meanwhile, a PPG signal for training may comprise baseline noise due to the movement of the subject to be measured (e.g., a patient). Since this noise may act as a factor that reduces accuracy in blood pressure estimation through the CFR model, the processor may remove the noise contained in the PPG signal for training.

Referring to FIG. 3, in one example, the processor may pass a PPG signal for training through a high pass filter (HPF) to remove baseline noise from the PPG signal for training, and at this time, the cutoff frequency of the high pass filter may be set to 40 Hz.

Hereinafter, the process by which the processor extracts various blood flow characteristics from the PPG signals for training will be described in detail.

The processor may first sample the PPG signals for training at preset unit time intervals (e.g., 5 seconds). Referring again to FIG. 2A, the processor may apply a sliding window to the PPG signals for training and sample the PPG signals for training every 5 seconds (Ts).

Subsequently, the processor may detect the R-R intervals and heart rate variability (HRV) from the sampled signals.

Taking FIG. 4 as an example, the processor may detect the R-peaks of the sampled signals and detect the intervals between adjacent R-peaks, i.e., the R-R intervals (RRs). Further, the processor may detect heart rate variability (RRdiff) based on the difference between adjacent R-R intervals (RRs).

The processor may extract a plurality of blood flow characteristics based on the previously detected R-R intervals (RRs) and heart rate variability (RRdiff).

In one example, the blood flow characteristics of the present invention may comprise BPM, SDNN, RMSSD, IBI, and SDSD defined by [Table 1] below.

TABLE 1

| Blood characteristic | Definition |
| --- | --- |
| BPM | $\dfrac{60000 \text{ ms(1 minute)}}{\overline{RR}}$ |
| SDNN | $\sqrt{\dfrac{1}{n-1}\sum_{i=1}^{n}(RR_i - \overline{RR})^2}$ |
| RMSSD | $\sqrt{\dfrac{1}{n-1}\sum_{i=1}^{n}(RRdiff_i)^2}$ |
| IBI | $\dfrac{1}{n-1}\sum_{i=1}^{n} RR_i$ |
| SDSD | $\sqrt{\dfrac{1}{n-1}\sum_{i=1}^{n}(RRdiff_i - \overline{RRdiff})^2}$ |

(wherein $RR_i$ is the sequentially indexed R-R interval in the sampled signal, n is the number of $RR_i$ in the sampled signal, and $RRdiff_i$ is the heart rate variability sequentially indexed in the sampled signal.)

In another example, the blood flow characteristics of the present invention essentially comprise the elements of [Table 1] described above, and the plurality of blood flow characteristics further comprise at least one of SD1, SD2, S, SD, pNN20, pNN50 and HR mad defined by [Table 2] below.

TABLE 2

| Blood characteristic | Definition |
|---|---|
| SD1 | $\sqrt{\frac{1}{2}SDSD^2}$ |
| SD2 | $\sqrt{2SDNN^2 - \frac{1}{2}SDSD^2}$ |
| S | $\pi \times SD1 \times SD2$ |
| SD | SD1/SD2 |
| pNNxx | $\frac{RR_x}{n}$ |
| HR mad | median($|RR_i - $median$(RR)|$) |

(wherein $RR_x$ is the number of $RR_i$ with an interval of x or more.)

As described above, the processor may extract a maximum of 12 blood flow characteristics from the PPM signals for training, and the extraction operation may be performed for each sample.

Next, the process by which the processor calculates systolic and diastolic blood pressures from ambulatory blood pressures for training will be explained in detail.

The processor may first sample the ambulatory blood pressures for training at preset unit time intervals (e.g., 5 seconds). Referring again to FIG. 2B, the processor may apply a sliding window to the ambulatory blood pressures for training to sample the ambulatory blood pressures for training every 5 seconds (Ts). At this time, the unit time may be the same as the unit time for previously sampling the PPG signals for training.

The processor may then detect a plurality of high peaks and a plurality of low peaks in the sampled signals.

Referring to FIG. 5A, the processor may detect a high peak for each sampled periodic signal. At this time, in order to remove noise that may be contained in the ambulatory blood pressures, the processor may only detect high peaks above the reference value. For example, the processor may only detect high peaks above 80 mmHg.

Further, referring to FIG. 5B, the processor may detect a low peak for each sampled periodic signal. Likewise, in order to remove noise that may be contained in the ambulatory blood pressures, the processor may only detect low peaks above a reference value. For example, the processor may only detect low peaks above 40 mmHg.

Subsequently, the processor may calculate systolic and diastolic blood pressures by averaging out the plurality of high peaks and the plurality of low peaks, respectively. For example, in FIG. 5A, the processor may average out five high peaks to calculate a systolic blood pressure, and, in FIG. 5B, the processor may average out five low peaks to calculate a diastolic blood pressure.

Meanwhile, in order to utilize only high-quality training data for training the CFR model, the processor may exclude the corresponding samples from the training data in the cases that the number of the peaks detected in the PPG signals for training is different from the number of the high peaks detected in the ambulatory blood pressures for training, or the numbers of high and low peaks detected in the ambulatory blood pressures for training are different from each other.

When a training dataset is constructed according to the above-described method, the processor may train a CFR model by labeling systolic and diastolic blood pressures to a plurality of blood flow characteristics S30.

The training dataset may comprise a plurality of blood flow characteristics previously extracted as input data, and may comprise previously calculated systolic and diastolic blood pressures as a label (ground truth (GT)). The processor may perform supervised training of the CFR model so that the CFR model receives multiple blood flow characteristics and outputs systolic and diastolic blood pressures.

Specifically, the processor may input a plurality of blood flow characteristics into the CFR model and supervised train the CFR model so that the difference between the predicted values output from the CFR model and the labeled systolic and diastolic blood pressures is minimized. To this end, the processor may generate a first objective function proportional to |Predicted Systolic Blood Pressure-Labeled Systolic Blood Pressure|, and a second objective function proportional to |Predicted Diastolic Blood Pressure-Labeled Diastolic Blood Pressure|, and train the CFR model such that each of the first and second objective functions is minimized.

Referring to FIG. 6, the CFR model 100 according to an embodiment of the present invention may comprise a plurality of layers (layers 1 to n) and an end layer connected to the rear end. At this time, each layer may comprise a plurality of random forests and a plurality of extra trees, for example, two random forests and two extra trees.

The random forests may bootstrap sample a preset number of blood flow characteristics under the control of the processor and generate multiple decision trees, thereby outputting predicted values of systolic and diastolic blood pressures. At this time, the splitting variable and splitting point of each decision tree contained in a random forest may be determined through training.

On the other hand, the extra trees may use all of the plurality of blood flow characteristics as training data under the control of the processor without using bootstrap sampling to generate multiple decision trees, thereby outputting predicted values of systolic and diastolic blood pressures. Likewise, the splitting variables and splitting points of each decision tree contained in each extra tree may be determined through training.

Hyperparameters of the above-described CFR model 100 may be illustratively set as shown in [Table 3] below.

TABLE 3

| [Hyperparameters] | [Details] | [Value] |
|---|---|---|
| n_estimators | The number of decision trees in a random forest | 100 |
| min_samples_split | The number of sample blood flow characteristics for node splitting of a decision tree | 20 |
| max_features | The maximum number of blood flow characteristics to be considered for optimal splitting | Sqrt($f_n$) OR log2($f_n$) |

(wherein $f_n$ is the total number of blood flow characteristics used for training the CFR model 100.)

Referring again to FIG. 6, a plurality of layers contained in the CFR model 100 may be sequentially connected, and the predicted values output from the previous layer may be combined with the blood flow characteristics input into the first CFR model 100 and input into the next layer.

Specifically, 12-dimensional blood flow characteristics may be input into the first layer of the CFR model 100. Each of the two random forests and two extra trees that constitute the first layer may extract and output predicted values (features), and the output 4-dimensional predicted values may be combined with the 12-dimensional blood flow characteristics that were initially input into the CFR model 100 and input into the second layer.

Likewise, each of the two random forests and two extra trees that constitute the second layer may extract and output predicted values (features), and the output 4-dimensional predicted values may be combined with the 12-dimensional blood flow characteristics that were initially input into the CFR model 100, and input into the third layer.

Such extraction and combination operations of characteristics may be repeated through layers, and the average value of the 4-dimensional characteristics output from the two random forests and two extra trees that constitute the end layer may be set as systolic or diastolic blood pressures.

Meanwhile, the larger the number of layers constituting the CFR model 100, the better the training performance. However, for fast training speed and lightweight of the model 100, the number of layers increases only until the accuracy of the CFR model 100 becomes sufficient. To this end, the processor may evaluate the performance of the CFR model 100 for each number of layers through the verification dataset and determine the number of layers based on the evaluated performance.

Specifically, the processor may construct a part of the PPG signals for training and a part of the ambulatory blood pressures for training as a validation dataset, and calculate the accuracy of the CFR model 100 through them. The processor may then compare the calculated accuracy to a reference value and add a layer to the CFR model 100 only if the accuracy is less than the reference value. At this time, the processor may compare the prediction accuracy for the systolic blood pressure and the prediction accuracy for the diastolic blood pressure with a reference value, and, if either is less than the reference value, a layer may be added to the CFR model 100.

Taking FIG. 7 as an example, the processor may train the CFR model 100 comprising only a single layer through a training dataset and then calculate accuracy, for example, the $R^2$ coefficient of determination, using a validation dataset. The processor may calculate prediction accuracies for systolic and diastolic blood pressures of the corresponding CFR model 100 as 0.73 and 0.71, respectively, and compare them with a reference value (e.g., 0.85).

Since both prediction accuracies are below the reference value, the processor may add a layer to the CFR model 100 and calculate the accuracy of the CFR model 100 in the same manner as the previous method. The processor may calculate the prediction accuracies for systolic and diastolic blood pressures of the CFR model 100 comprising two layers as 0.855 and 0.83, respectively. Since either prediction accuracy is below the reference value (e.g., 0.85), the processor may add a layer to the CFR model 100.

Subsequently, the processor may calculate the prediction accuracies for systolic and diastolic blood pressures of the CFR model 100 comprising three layers as 0.87 and 0.845, respectively. Since either prediction accuracy is below the reference value (e.g., 0.85), the processor may add a layer to the CFR model 100.

The prediction accuracy for systolic and diastolic blood pressures of the CFR model 100 comprising four layers may finally be calculated above the reference value (e.g., 0.85), and, at this time, the processor may not add any more layers to the CFR model 100.

When training of the CFR model 100 is completed according to the above-described method, the processor may determine the systolic and diastolic blood pressures of the target user by inputting the PPG signals of the target user into the CFR model 100 $40.

Through the previous training process, the CFR model 100 may learn the relationships between multiple blood flow characteristics and systolic and diastolic blood pressures. Accordingly, the CFR model 100 to which arbitrary blood flow characteristics that were not used for training may be input into output systolic and diastolic blood pressures corresponding to them.

In one embodiment, the processor may first collect the PPG signals of a target user to predict blood pressure. For example, the processor may collect the target user's PPG signals from any sensor capable of photoplethysmography. For example, the processor may collect the target user's PPG signals by wirelessly communicating with a wearable device equipped with a photoplethysmography sensor.

Subsequently, the processor may pass the collected PPG signals through a high-pass filter (HPF) to remove baseline noise, and sample the noise-removed PPG signals at unit time intervals. At this time, the sampled unit time interval may be the same as the time interval (e.g., 5 seconds) of the sample used as training data for the CFR model 100.

Subsequently, the processor may extract a plurality of target blood flow characteristics from the sampled signals. At this time, the method of extracting the target blood flow characteristics may be the same as the method described in step S12.

Subsequently, the processor may input the target blood flow characteristics into the CFR model 100, and determine the predicted values output from the CFR model 100 as the systolic and diastolic blood pressures of the target user.

As described above, the present invention estimates blood pressures from PPG signals using the CFR model 100, thereby enabling users to self-measure blood pressures in their daily lives non-invasively and easily.

As described above, the present invention has been described with reference to the illustrative drawings, but the present invention is not limited to the embodiments and drawings disclosed herein, and it is obvious that various modifications may be made by those skilled in the art within the scope of the technical idea of the present invention. Further, even if the effects of the features of the present invention were not explicitly described and explained while explaining the above embodiments of the present invention, it is natural that the predictable effects from the features should also be recognized.

What is claimed is:

1. A blood pressure estimation method using a cascade forest regression model comprising:
    extracting a plurality of blood flow characteristics from PPG signals for training,
    calculating systolic and diastolic blood pressures from ambulatory blood pressures for training,
    labeling the systolic and diastolic blood pressures with the plurality of blood flow characteristics to train a cascade forest regression model, and
    inputting the PPG signals of a target user into the trained cascade forest regression model to determine the systolic and diastolic blood pressures of the target user.

2. The blood pressure estimation method using a cascade forest regression model of claim 1,
wherein the step of extracting a plurality of blood flow characteristics comprises
passing the PPG signals for training through a high pass filter (HPF) to remove noise from the PPG signals for training.

3. The blood pressure estimation method using a cascade forest regression model of claim 1,
wherein the step of extracting a plurality of blood flow characteristics comprises
sampling the PPG signals for training at unit time intervals,
detecting R-R interval and heart rate variability (HRV) from the sampled signals, and
extracting the plurality of blood flow characteristics based on the R-R interval and heart rate variability.

4. The blood pressure estimation method using a cascade forest regression model of claim 3,
wherein the plurality of blood flow characteristics comprise BPM, SDNN, RMSSD, IBI and SDSD defined by the following equations:

$$BPM = \frac{60000 \text{ ms}(1 \text{ minute})}{\overline{RR}}$$

$$SDNN = \sqrt{\frac{1}{n-1}\sum_{i=1}^{n}(RR_i - \overline{RR})^2}$$

$$RMSSD = \sqrt{\frac{1}{n-1}\sum_{i=1}^{n}(RRdiff_i)^2}$$

$$IBI = \frac{1}{n-1}\sum_{i=1}^{n}RR_i$$

$$SDSD = \sqrt{\frac{1}{n-1}\sum_{i=1}^{n}(RRdiff_i - \overline{RRdiff})^2}$$

in which $RR_i$ is the sequentially indexed R-R interval in the sampled signal, n is the number of $RR_i$ in the sampled signal, and $RRdiff_i$ is the heart rate variability sequentially indexed in the sampled signal.

5. The blood pressure estimation method using a cascade forest regression model of claim 4,
wherein the plurality of blood flow characteristics further comprise at least one of SD1, SD2, S, SD, pNN20, pNN50 and HR mad defined by the following equations:

$$SD1 = \sqrt{\frac{1}{2}SDSD^2}$$

$$SD2 = \sqrt{2SDNN^2 - \frac{1}{2}SDSD^2}$$

$$S = \pi \times SD1 \times SD2$$

$$SD = SD1/SD2$$

$$pNNxx = \frac{RR_x}{n}$$

$$HR \text{ mad} = \text{median}(|RR_i - \text{median}(RR)|)$$

in which $RR_x$ is the number of $RR_i$ with an interval of x or more.

6. The blood pressure estimation method using a cascade forest regression model of claim 1,
wherein the step of calculating the systolic and diastolic blood pressures comprises:
sampling the ambulatory blood pressures for training at unit time intervals,
detecting a plurality of high peaks and a plurality of low peaks in the sampled signals, and
averaging out the plurality of high peaks and the plurality of low peaks, respectively, to calculate the systolic and diastolic blood pressures.

7. The blood pressure estimation method using a cascade forest regression model of claim 6,
wherein the step of detecting the plurality of high peaks and the plurality of low peaks comprises
detecting only peaks above a reference value.

8. The blood pressure estimation method using a cascade forest regression model of claim 1,
wherein the step of training the cascade forest regression model comprises:
inputting the plurality of blood flow characteristics into the cascade forest regression model, and
supervising training the cascade forest regression model such that the difference between the predicted values output from the cascade forest regression model and the labeled systolic and diastolic blood pressures is minimized.

9. The blood pressure estimation method using a cascade forest regression model of claim 1,
wherein the cascade forest regression model comprises a plurality of layers, and each of the plurality of layers comprises a plurality of random forests and a plurality of extra trees.

10. The blood pressure estimation method using a cascade forest regression model of claim 1,
wherein the cascade forest regression model comprises a plurality of sequentially connected layers, and the predicted values output from the previous layer is combined with the blood flow characteristics and input into the next layer.

11. The blood pressure estimation method using a cascade forest regression model of claim 1,
wherein the cascade forest regression model comprises a plurality of sequentially connected layers, and
the step of training the cascade forest regression model comprises calculating the accuracy of the cascade forest regression model through a validation dataset comprising a portion of the PPG signals for training and a portion of the ambulatory blood pressures for training, and adding a layer to the cascade forest regression model if the accuracy is less than a reference value.

12. The blood pressure estimation method using a cascade forest regression model of claim 1,
wherein the step of determining the systolic and diastolic blood pressures of the target user comprises:
collecting the PPG signals of the target user,
sampling the PPG signals at unit time intervals,
inputting the sampled signals into the cascade forest regression model, and
determining the predicted values output from the cascade forest regression model as the systolic and diastolic blood pressures of the target user.

* * * * *